US010201768B2

(12) United States Patent
Eriksson et al.

(10) Patent No.: US 10,201,768 B2
(45) Date of Patent: Feb. 12, 2019

(54) ADAPTOR FOR A CHROMATOGRAPHY COLUMN (71) Applicant: GE Healthcare Bio-Sciences AB, Uppsala (SE)

(72) Inventors: Stefan Kjell Eriksson, Uppsala (SE); Andreas Bergstrom, Uppsala (SE)

(73) Assignee: GE HEALTHCARE BIO-SCIENCES AB, Uppsala (SE)

( * ) Notice: Subject to any disclaimer, the term of this patent is extended or adjusted under 35 U.S.C. 154(b) by 498 days.

(21) Appl. No.: 14/409,593

(22) PCT Filed: Jun. 18, 2013

(86) PCT No.: PCT/SE2013/050711
§ 371 (c)(1),
(2) Date: Dec. 19, 2014

(87) PCT Pub. No.: WO2013/191628
PCT Pub. Date: Dec. 27, 2013

(65) Prior Publication Data
US 2015/0321121 A1    Nov. 12, 2015

(30) Foreign Application Priority Data
Jun. 21, 2012   (SE) ...................................... 1250668

(51) Int. Cl.
*B01D 15/22*    (2006.01)
*G01N 30/56*    (2006.01)
(Continued)

(52) U.S. Cl.
CPC ............. *B01D 15/22* (2013.01); *B01D 35/02* (2013.01); *G01N 30/56* (2013.01);
(Continued)

(58) Field of Classification Search
CPC ........ B01D 15/10; B01D 15/22; G01N 30/60; G01N 30/6004; G01N 30/6026; G01N 30/603; G01N 30/6017; G01N 30/6047
See application file for complete search history.

(56) References Cited

U.S. PATENT DOCUMENTS 3,483,986 A * 12/1969 Wright ............. G01N 27/44756
210/198.2
4,676,898 A *  6/1987 Saxena ................... B01D 15/14
210/198.2
(Continued)

FOREIGN PATENT DOCUMENTS

CN        1387038 A      12/2002
CN      200948371 Y      9/2007
(Continued)

OTHER PUBLICATIONS

International Search Report and Written Opinion dated Oct. 17, 2013 which was issued in connection with PCT Patent Application No. SE2013/050711 which was filed on Jun. 18, 2013.
(Continued)

*Primary Examiner* — Katherine Zalasky
(74) *Attorney, Agent, or Firm* — Wood IP LLC (57) ABSTRACT

An adaptor for a chromatography column, the adaptor comprising a substantially circular bottom plate provided with an end surface; a ring shaped wall element arranged at the periphery of the bottom plate. The bottom plate and the wall element having a common axis and the adaptor is provided with a filter connection arrangement for removably connecting a filter on the end surface of the bottom plate of the adaptor.

14 Claims, 9 Drawing Sheets

(51) Int. Cl.
*G01N 30/60* (2006.01)
*B01D 35/02* (2006.01)

(52) U.S. Cl.
CPC ..... *G01N 30/6004* (2013.01); *G01N 30/6017* (2013.01); *G01N 30/6021* (2013.01); *G01N 30/6047* (2013.01)

(56) References Cited

U.S. PATENT DOCUMENTS

| | | | | |
|---|---|---|---|---|
| 4,719,011 A * | 1/1988 | Shalon | ............... | B01D 15/14 210/198.2 |
| 4,797,209 A * | 1/1989 | Jackson | ............... | B01D 15/08 210/198.2 |
| 5,141,635 A * | 8/1992 | LePlang | ............... | B01D 15/08 210/198.2 |
| 5,169,522 A * | 12/1992 | Shalon | ............... | B01D 15/08 210/198.2 |
| 5,462,659 A * | 10/1995 | Saxena | ............... | B01D 15/18 210/198.2 |
| 6,190,560 B1 * | 2/2001 | Mann | ............... | B01D 15/206 210/198.2 |
| 6,984,318 B2 * | 1/2006 | Gill | ............... | B01D 15/22 210/198.2 |
| 7,718,058 B2 | 5/2010 | Agee et al. | | |
| 8,128,816 B2 | 3/2012 | Snyder | | |
| 8,394,276 B2 | 3/2013 | Eriksson | | |
| 2003/0173279 A1 * | 9/2003 | Aste | ............... | B01D 15/20 210/198.2 |
| 2003/0205515 A1 * | 11/2003 | Purdom | ............... | G01N 30/6026 210/198.2 |
| 2008/0264837 A1 | 10/2008 | Agee et al. | | |
| 2008/0308498 A1 * | 12/2008 | Davis | ............... | B01D 15/10 210/656 |
| 2013/0240426 A1 * | 9/2013 | Ramakrishna | ............... | B01D 15/22 210/198.2 |

FOREIGN PATENT DOCUMENTS

| | | |
|---|---|---|
| CN | 101489637 A | 7/2009 |
| EP | 0296624 A2 | 12/1988 |
| EP | 1396721 A1 | 3/2004 |
| EP | 2235522 A1 | 10/2010 |
| EP | 2139572 A1 | 4/2012 |
| EP | 2442878 A1 | 4/2012 |
| GB | 240244 A | 1/2008 |
| JP | 63173960 A | 7/1988 |
| JP | 2010-525370 A | 7/2010 |
| JP | 2011-510322 A | 3/2011 |
| JP | 5328765 B2 | 10/2013 |
| JP | 5620480 B2 | 11/2014 |
| WO | 2005056156 A1 | 6/2005 |
| WO | WO2007/050416 A2 | 5/2007 |
| WO | 2008/134413 A1 | 11/2008 |
| WO | WO2009/041877 A1 | 4/2009 |
| WO | 2009093952 A1 | 7/2009 |
| WO | 2010/132011 A1 | 11/2010 |
| WO | 2010147884 A1 | 12/2010 |
| WO | 2012074464 A1 | 6/2012 |
| WO | 2013/191628 A1 | 12/2013 |

OTHER PUBLICATIONS

Swedish Office Action dated Jan. 10, 2013 which was issued in connection with Swedish Patent Application No. SE1250668-9 which was filed on Jun. 21, 2012. An English translation of this document has been provided.
EP Search Report in corresponding EP Application No. 138077193.1 dated Jun. 3, 2016.
Office Action Received for Chinese Patent Application No. 201380032173.5, dated Feb. 4, 2017, 11 pages. (Official Copy 6 Pages+English Translation 5 pages.).
Office Action Received for Japanese Patent Application No. 2015-518372, dated Feb. 14, 2017, 6 pages. (Official Copy 2 Pages+ English Translation 4 pages.).
International Preliminary Report on Patentability Received for PCT Patent Application No. PCT/SE2013/050711, dated Dec. 23, 2014, 2 pages.
Office Action Received for Chinese Patent Application No. 201380032173.5, dated Oct. 9, 2017, 11 pages (5 Pages English Translation + 6 Pages Official Copy).

* cited by examiner

ADAPTOR FOR A CHROMATOGRAPHY COLUMN

CROSS-REFERENCE TO RELATED APPLICATIONS

This is a national stage application under 35 U.S.C. § 371(c) of prior-filed, co-pending, PCT application serial number PCT/SE2013/050711, filed on Jun. 18, 2013, which claims priority to Swedish patent application serial number 1250668-9, filed on Jun. 21, 2012, the entire contents of which are incorporated by reference herein.

TECHNICAL FIELD

Embodiments of the present invention relate to an adaptor for a chromatography column.

Adaptors for chromatography columns are used together with a filter and a distributor plate for packing a bed of packing material within the chromatography column. The distributor plate distributes fluid within column and the filter prevents particles from the bed of packing material to enter into holes or openings within the distributor plate and thereby the filter prevents the particles from escaping the column. Performing maintenance on chromatography columns, especially columns in industrial-scale chromatography, is necessary for cleaning and replacing bed supports, distributor plates and sliding rings. Heavy lifting equipment such as hoists or cranes to dismantle the columns has an influence on safety and time efficiency when performing maintenance. Embodiments of the invention are concerned with efficient and safer methods for performing maintenance on such columns.

BACKGROUND ART

The chromatography technique is widely used in different forms for separating chemical and biological substances and there are many applications in compound preparation, purification and analysis. Liquid chromatography is of particular importance in the pharmaceutical and biological industries for the preparation, purification and analysis of proteins, peptides and nucleic acids.

A typical liquid chromatography apparatus has an upright housing in which a bed of packing material, which is usually particulate in nature and consists of a porous medium, rests against a permeable retaining layer. A liquid mobile phase enters through an inlet, for example at the end of an adaptor rod which has an elongated extension within the column. The liquid mobile phase thereafter enters a distributor plate which distributes the liquid mobile phase through a porous, perforated filter, mesh, frit or net, which together with the distributor plate is arranged on an adaptor. The liquid mobile phase thereafter moves through the bed of packing material and is finally removed via an outlet, typically through a second filter, mesh, frit or net and a second distributor plate.

Columns used in liquid chromatography typically comprise a tubular body enclosing the porous chromatography medium through which the carrier liquid or mobile phase flows, with separation of substances or analytes taking place between the mobile phase and solid phase of the porous medium. Typically, the porous medium is enclosed in the column as a packed bed, generally formed by consolidating a suspension of discrete particles, known as slurry that is pumped, poured or sucked into the column, usually from a bore or nozzle located at a tubular housing or at one end of the column. The production of a stable, even bed is often critical to the final separation process.

Another critical feature in the separation of substances is the fluid distribution system, particularly as the cross-section of the chromatographic column increases. The efficiency of the chromatographic separation relies on the liquid distribution and collection system at the fluid inlet and outlet of the packed bed. Ideally, the carrier liquid is uniformly introduced throughout the surface at the top of the packing, flows through the packing at the same velocity throughout the packing cross section, and is uniformly removed at the plane defined by the bottom of the packed bed.

Conventional distribution systems for use in liquid chromatography comprise a distributor plate attached to the net. The distributor plate comprises channels arranged in a pattern to substantially uniform distribute the fluid over the plate. The distributor plate is perforated with holes or openings which lead the fluid from the channels and uniformly into the packed bed.

Applying a sample volume simultaneously over the cross-sectional area of the packed bed is critical for the result of the chromatography process. Un-uniform distribution of the sample volume will lead to increased dispersion in the chromatographic system by broadening the convective residence time distribution of a tracer substance transported with the fluid throughout the system. The dispersion generated by the liquid distribution system has to be controlled in relation to the amount of dispersion introduced by the chromatographic packed bed itself by means of diffusion and mixing effects. Without a simultaneous introduction of fluid in the plane defined by the top of the bed, it is virtually impossible to achieve so-called plug-flow behavior, which is a uniform and well-defined movement of the sample through the packed bed and column, respectively, resulting in a uniform residence time distribution.

During the chromatography process the packed bed may be damaged and fines may occur in the column. After several chromatography cycles the fines may clog the net or nets in the column, which may result in higher back pressure and lower process efficiency. Therefore, the nets must be replaced after a number of cycles.

According to known chromatography columns the nets are welded or heat shrinked on the distributor plate, which distributor plate in turn is removably connected by fastening elements on the adaptor. Time and cost consuming operations are necessary in order to remove the clogged net from the distributor plate. Especially, when the chromatography column is of a large size the removal of the net from the distributor plate by using milling or turning machines is complicated. The replaced net must be welded or heat shrinked on the distributor plate before remounting on the adaptor. The chromatography column may not be used under a substantially period of time during the replacement of the nets. This may lead to production losses in the pharmaceutical and biological industries.

Also, compression fluid held within the column above the adaptor must be drained from the column before replacing the filter on the adaptor. Draining the column of compression fluid is time consuming and requires special equipment.

Document WO2010/132011A1 discloses a chromatography column provided with an adaptor, a filter and a distributor plate. Notwithstanding the existence of such prior art, there is a need to improve the maintenance methods available for chromatography columns by providing columns which are safer and easier for operators to use. Also, there is a need to reduce cost and time when conducting maintenance on chromatography columns. Also, there is a need to reduce complexity and to reduce needed floor space when conducting maintenance on chromatography columns. There is also a need for an improved and more efficient filter that is easy, fast and safe to replace. Because the filter is in contact with fluid used in a chemical process it is also important that the filter is easy to clean.

SUMMARY OF THE INVENTION

An objective problem to be solved by the present invention is to achieve an adaptor for a chromatography column, which makes it easy, fast and safe to conduct maintenance on chromatography columns.

Another objective problem to be solved by the present invention is to reduce cost when conducting maintenance on chromatography columns.

These objects above are achieved by an adaptor for a chromatography column according to claim 1.

When the adaptor is provided with a filter connection arrangement for removably connecting a filter on the end surface of the bottom plate of the adaptor maintenance on the chromatography column is easy, fast and safe to conduct. There is no need to drain the compression fluid held within the column above the adaptor before replacing the filter on the adaptor. As a result, when conducting maintenance on chromatography columns, cost will be reduced.

According to an embodiment of the invention the filter connection arrangement is at least one cavity arranged in the periphery of the adaptor. When conducting maintenance on the column a part of the adaptor assembly may still be within the tubular housing of the column, so that the compression fluid held within the column above the adaptor assembly cannot escape from the column. In this position the cavities arranged in a periphery of the adaptor assembly are positioned outside the tubular housing, so that it is possible to get access to the cavities from outside of the column. Thereafter fastening means are released trough the cavity for removing the filter from the adaptor assembly. As a result, maintenance on the chromatography column is easy, fast and safe to conduct. Also, cost will be reduced.

According to another embodiment of the invention the filter connection arrangement is a flange means arranged on the end surface of bottom plate, which flange means extends in the axial direction of the adaptor and which flange means is provided with fastening means. When conducting maintenance on the column a part of the adaptor assembly may still be within the tubular housing of the column, so that the compression fluid held within the column above the adaptor assembly cannot escape from the column. In this position it is possible to get access to and replace the filter from outside of the column by a helical thread or by a bayonet coupling arranged on the flange means and on the fixating means on the filter. As a result, maintenance on the chromatography column is easy, fast and safe to conduct. Also, cost will be reduced.

According to still another embodiment of the invention the filter arranged on the adaptor comprises a perforated net element and a fixating means attached to the net element, so that said fluid and particles are prevented to pass between the net element and the fixating means; and the fixating means is provided with at least one fastening element for removably fixating the filter to the adaptor. The removal of the fastening element by loosen the threaded bolt or a nut using for example a wrench will make the filter easy, fast and safe to replace.

Embodiments of the invention accordingly comprises the features of construction, combination of elements, and arrangement of parts that will be exemplified in the description set forth hereinafter and the scope of the invention will be indicated in the claims.

BRIEF DESCRIPTION OF THE DRAWINGS

Further aspects, advantages and features of the invention can be derived from the following detailed description of exemplary embodiments of the invention, with reference to the drawings.

DETAILED DESCRIPTION

Figure 1:
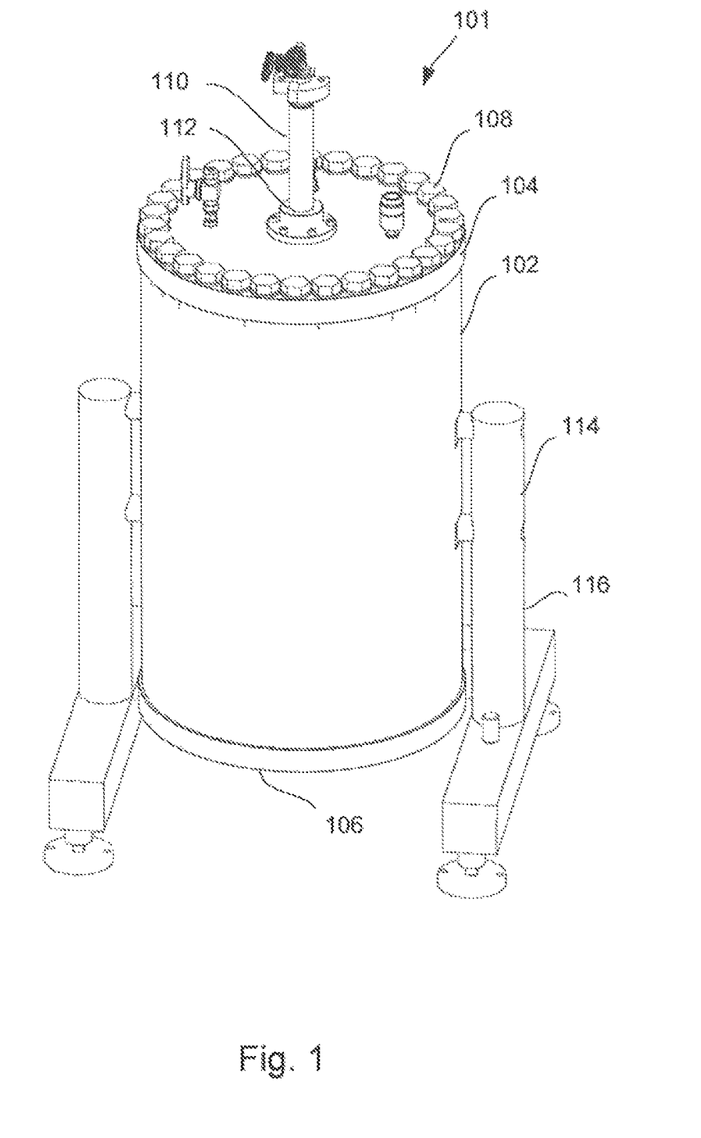
FIG. 1 shows a view in perspective of a chromatography column.

FIG. 1 shows a view in perspective of a chromatography column 101, which comprises a tubular housing 102, a first end unit 104 and a second end unit 106, secured together to form a fluid tight seal by means of tension bolts 108. The tubular housing 102 and end units 104, 106 are typically composed of stainless steel or a high-strength plastic material such as polypropylene. In an embodiment, where the column 101 is to be used for the separation of biologically active substances, the material is biologically inert such that it does not elicit an immune response in humans in accordance with United States Pharmacopia (USP)<88> class VI. An adaptor rod 110 extends through an opening 112 in the first end unit 104 and into the tubular housing 102. The column 101 is arranged on a frame 114 provided with legs 116, so that the column 101 may be placed on a floor in a stable position.

Figure 2:
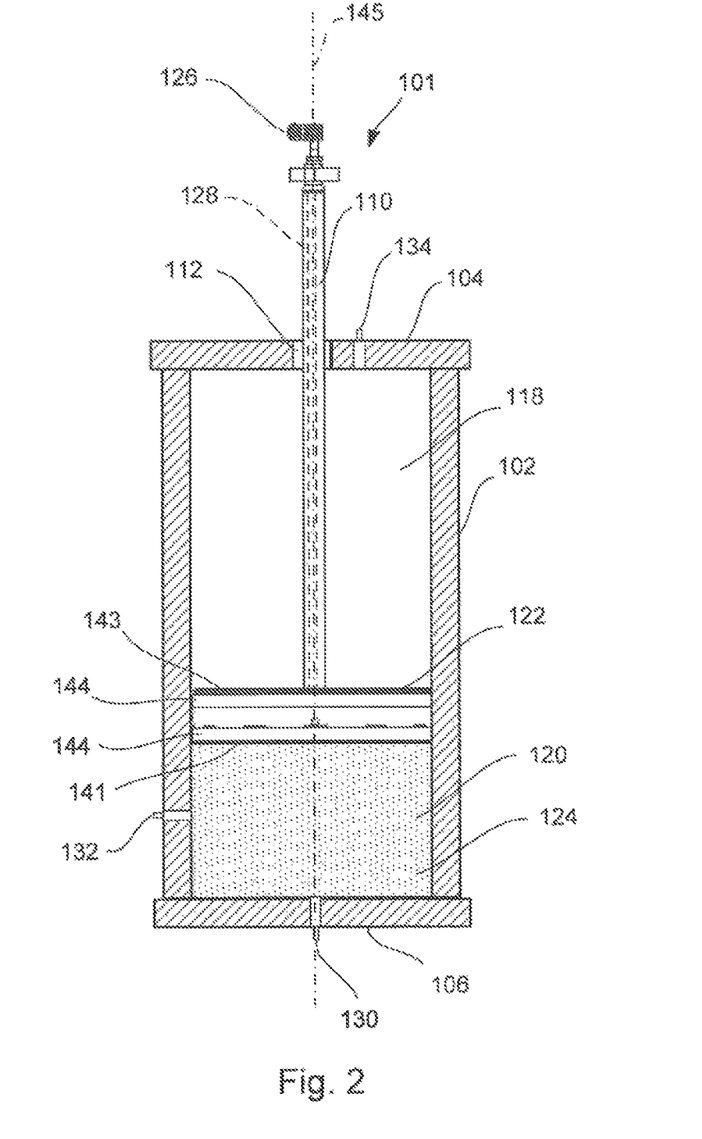
FIG. 2 shows a schematic section view of the chromatography column in FIG. 1.

FIG. 2 shows a schematic section view of the chromatography column 101 in FIG. 1.

The tubular housing 102 and the end units 104, 106 form a fluid space 118 and bed space 120, which spaces both are fluid tight and are capable of withstanding high operating pressures. A wide range of column capacities is possible, typically ranging from 0.1 to 2000 liters.

The bed space 120 is defined by the tubular housing 102, the second end unit 106 and an adaptor 122 connected to the adaptor rod 110. The bed space 120 is filled with a bed 124 of packing material, which is usually particulate in nature and consists of a porous medium. A liquid mobile phase is arranged to enter through an inlet 126 at the end of the adaptor rod 110 and flows through a central channel 128 in the adaptor rod 110 and further to the adaptor 122. The liquid mobile phase thereafter moves through the bed 124 of packing material and is finally removed via an outlet 130 in the second end unit 106. Typically, the porous medium enclosed in the column 101 as a packed bed 124 is generally formed by consolidating a suspension of discrete particles, known as slurry that is pumped, poured or sucked into the column 101 from a bore or nozzle 132 located at the tubular housing 102.

The bed 124 of packed particulate medium is obtained by the downward movement of the adaptor 122 to compress the bed 124 between the adaptor 122 and the second end unit 106. The compression force and downward movement of the adaptor 122 is achieved by a pressurized fluid in the fluid space above the adaptor 122. The fluid, e.g. water, is pumped into the column 101 from a valve 134 located at the first end unit 104.

Figure 3:
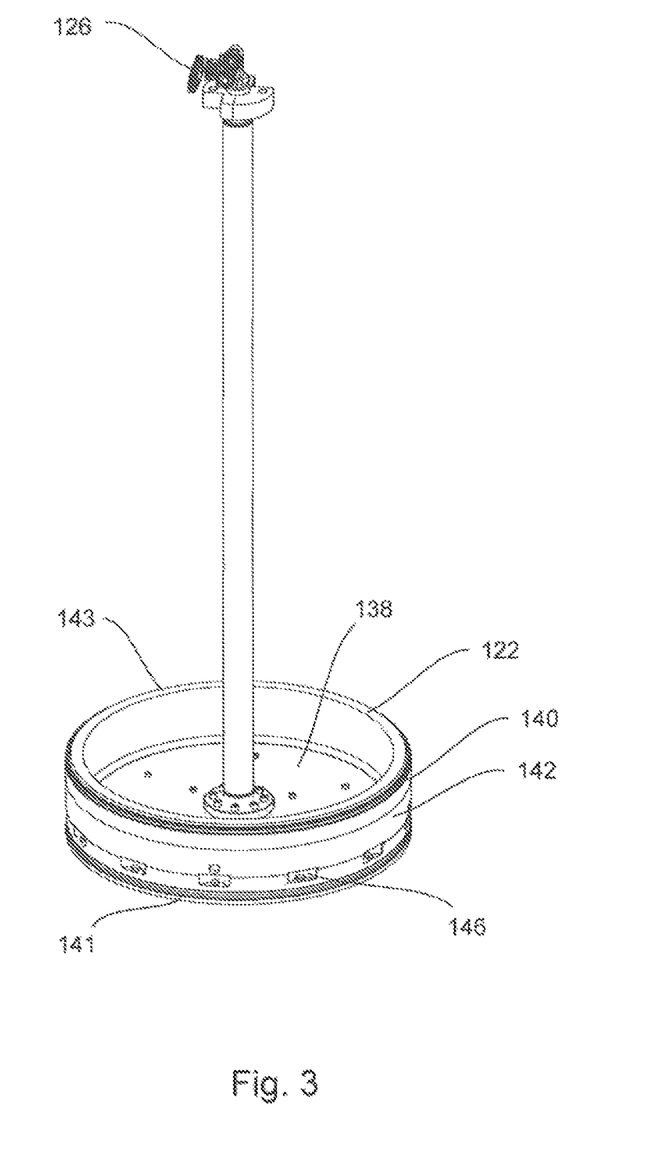
FIG. 3 shows a view in perspective of an adaptor assembly for a chromatography column according to a first embodiment of the invention.

FIG. 3 shows a view in perspective of an adaptor 122 provided with a chromatography column filter 136 according to an embodiment. The adaptor 122 has a substantially circular shape provided with a bottom plate 138 on which a ring shaped wall element 140 is arranged. The bottom plate 138 and wall element 140 may be made in one piece. It is also possible that the bottom plate 138 and wall element 140 are made in two pieces and that the wall element 140 is arranged at the bottom plate 138. The bottom plate 138 is provided with an end surface 141 and the wall element 140 has a top surface 143 which is directed substantially in an opposite direction to the end surface 141 of the bottom plate 138. The bottom plate 138 and the wall element 140 having a common axis 145, which, in an embodiment, is common to the axis of the adaptor rod 110. The peripheral outer surface 142 of the ring shaped wall element 140 is provided with sliding rings 144, which are arranged to slide against the inner surface of the tubular housing 102 of the chromatography column 101. The ring shaped wall element 140 has an essential extension in an axial direction of the adaptor 122. The axial extension of the ring shaped wall element 140 contributes to an axial stability of the adaptor 122 in the column 101, so that the surface of the bottom plate 138 always is parallel to the surface of the second end unit 106. As a result the compression of the packed bed 124 will be uniform, and the production of a stable, even bed 124 is often critical to the final separation process in the chromatography column 101. The adaptor 122 is provided with a filter connection arrangement for removably connecting the filter 136 on the end surface of the bottom plate 138 of the adaptor 122. According to a first embodiment of the invention the filter connection arrangement is a number of cavities 146 which are circumferentially and evenly arranged in the peripheral outer surface 142 of the ring shaped wall element 140 of the adaptor 122. The function of these cavities 146 will be described further below.

Figure 4:
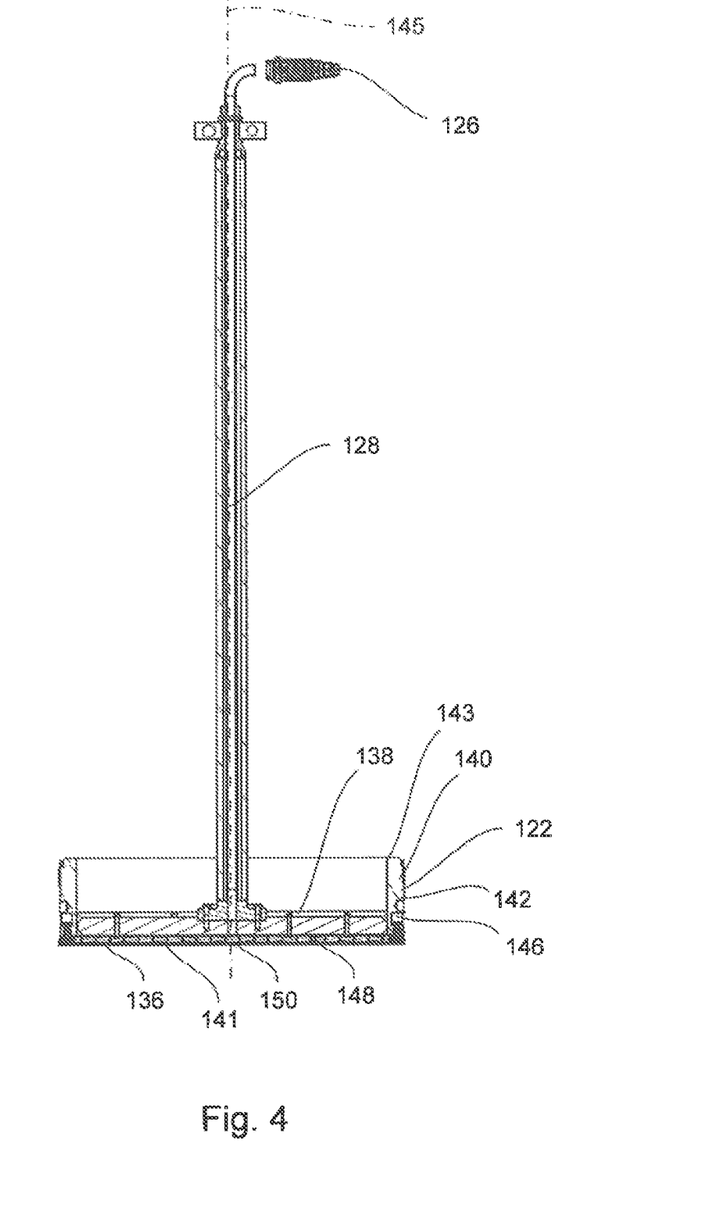
FIG. 4 shows a section view of an adaptor assembly for a chromatography column according to the first embodiment of the invention.
Figure 5:
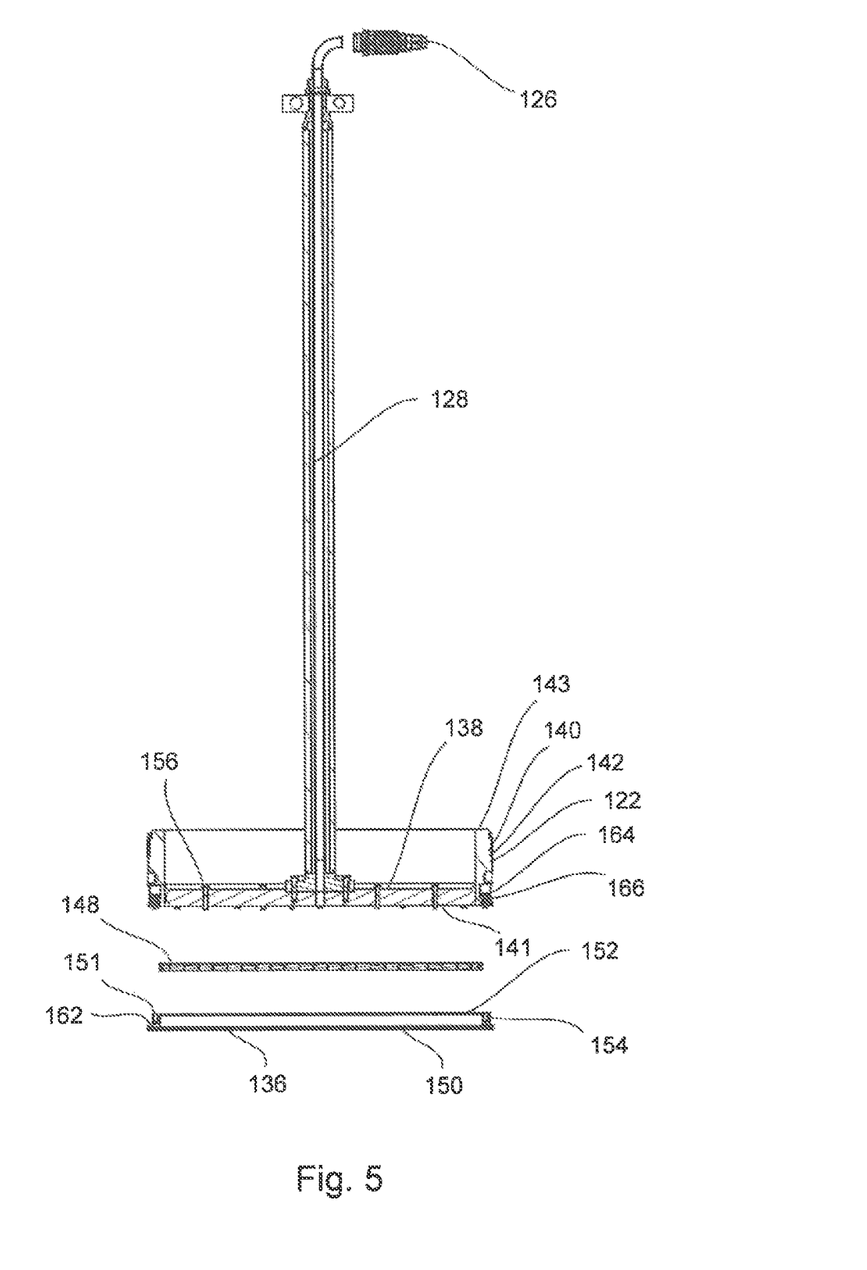
FIG. 5 shows a section view of an adaptor for a chromatography column according to the first embodiment of the invention, provided with a distributor plate and a filter.

FIGS. 4 and 5 show section views of an adaptor 122 according to an embodiment provided with a chromatography column filter 136. In FIG. 4 a distributor plate 148 and a chromatography column filter 136 are mounted on the adaptor 122. In FIG. 5 the distributor plate 148 and the filter 136 are separated from the adaptor 122. The chromatography column filter 136 comprising, a porous, perforated net element 150 through which fluid and particles up to a predetermined size are allowed to pass. A substantially circular, ring shaped fixating means 152 is attached to the net element 150. The fixating means 152 is provided with at least one fastening element 154, 254 for removably fixating the filter 136 to the adaptor 122 of the chromatography column 101, so that the filter 136 may be easy, fast and safe to replace. Also, the filter 136 is easy to clean when the filter 136 is removably fixated to the adaptor 122 by means of the fastening elements 154, 254.

A distributor plate 148 is removably connected to the bottom plate 138 of the adaptor 122 by means of fasteners 156. The distributor plate 148 comprises channels 158 arranged in a pattern to substantially uniform distribute the fluid over the plate 148. The distributor plate 148 is perforated with holes or openings 160 which lead the fluid from the channels 158 and uniformly into the packed bed 124. The filter 136 prevents particles from the bed 124 to enter into the holes or openings 160 within the distributor plate 148.

In an embodiment, the fixating means 152 is attached to the net element 150 by means of a weld 162, so that said fluid and particles are prevented to pass between the net element 150 and the fixating means 152. A tight and sealed connection is achieved by welding the fixating means 152 to the net element 150. When the fixating means 152 and the net element 150 are welded to one unit the replacement of the net element 150 will be easy, fast and safe.

The fastening element may be at least one threaded bore 154 in the fixating means 152. In an embodiment, several threaded bores 154 are evenly arranged in the ring shaped fixating means 152. Threaded bolts 164 are correspondingly arranged in the adaptor 122. The threaded bolts 164 removably fixate the fixating means 152 to the adaptor 122 and the removal of the threaded bolts 164 will make the replacement of the filter 136 easy, fast and safe. Each threaded bolt 164 is arranged in a cavity 146 in the periphery of the ring shaped wall element 140 of the adaptor 122. From each cavity 146 a bore 166 extends in an axial direction of the adaptor 122. The bore 166 is arranged between the cavity and the end surface of the bottom plate 138. The bores 166 extend in a direction substantially parallel to the axis 145. The cavities 146 and bores 166 make it possible to connect the fixating means 152 by means of the threaded bolts 164 which extend through the axial directed bores 166. Each cavity 146 has a depth and an extension in the circumferential direction of the adaptor 122 large enough to reach the head of the threaded bolt 164 by means of a tool, for example a wrench. The depth of the cavities 146, in a direction substantially perpendicular to the axis 145 corresponds to or exceeds the dimensions of a fastening element 164 inserted into the cavity. The length of the at least one cavity 146, in the axial direction of the adaptor 122, is less than the high of the wall element 140.

Figure 6:
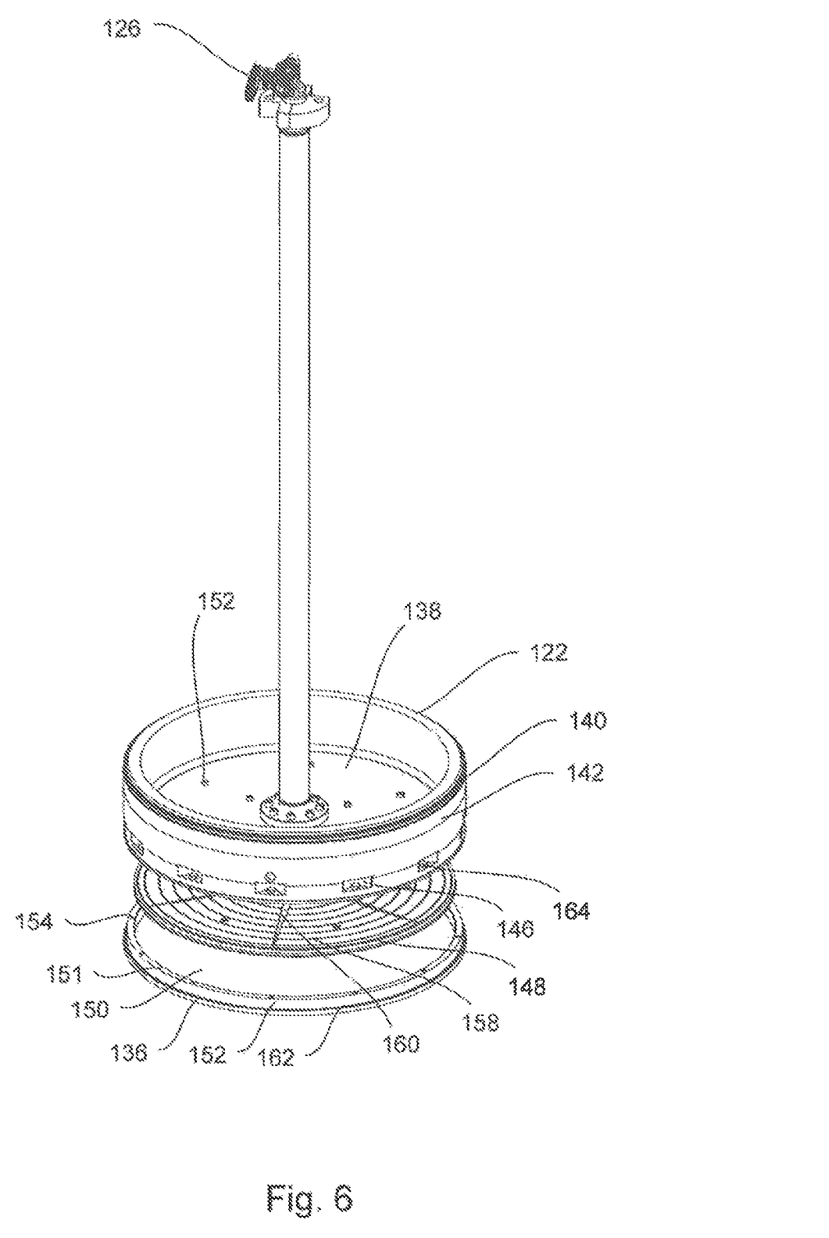
FIG. 6 shows a view in perspective of an adaptor for a chromatography column according to the first embodiment of the invention, provided with a distributor plate and a filter.

FIG. 6 shows a view in perspective of an adaptor 122, a distributor plate 148 and a chromatography column filter 136 according to an embodiment. The fixating means 152 is, in an embodiment, provided with a sealing surface 151, which together with a corresponding surface on the adaptor 122 prevents said fluid and particles to pass between the fixating means 152 and the adaptor 122. The sealing surface 151 contributes to the uniform distribution of carrier liquid throughout the surface at the top of the bed 124.

Figure 7:
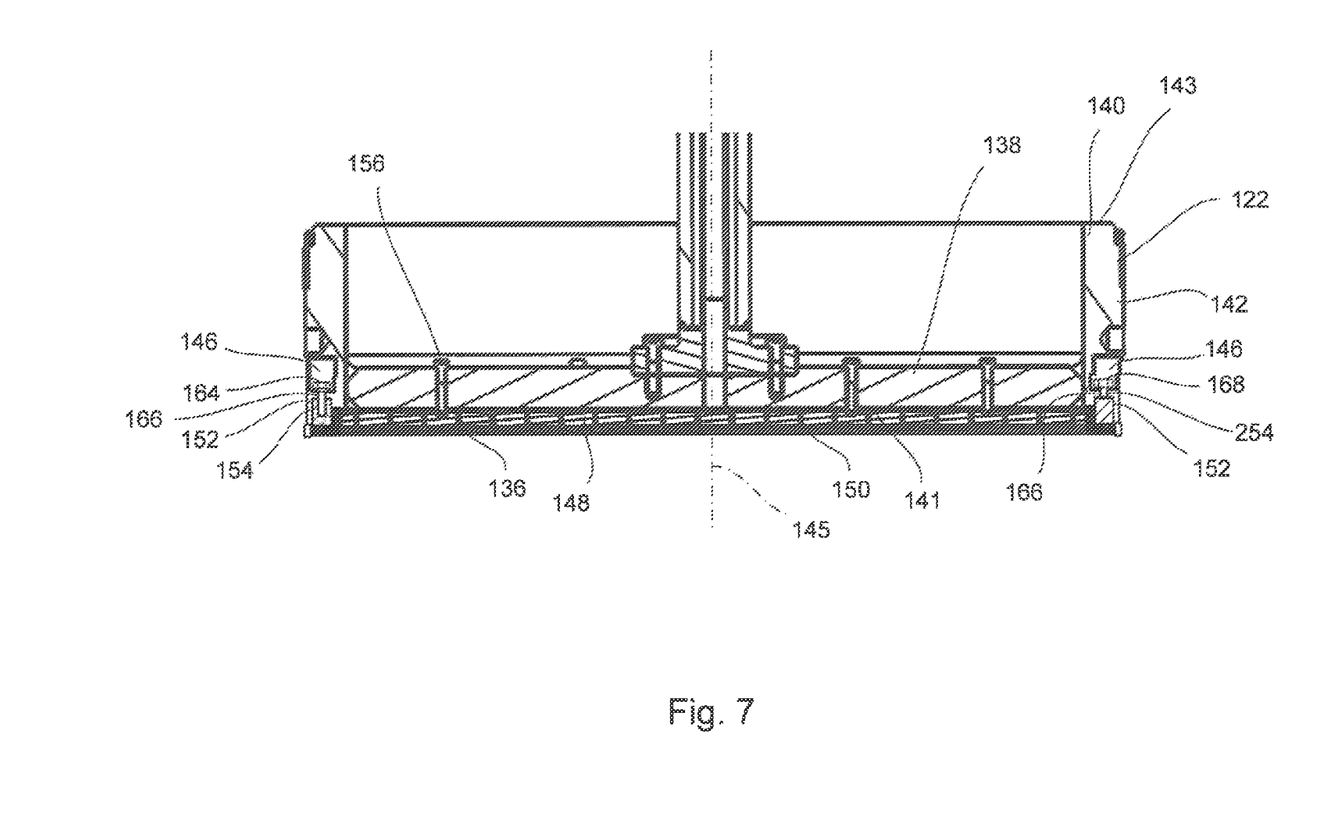
FIG. 7 shows a section view in detail of an adaptor according to the first embodiment of the invention.

As disclosed in FIG. 7 the fastening element may also be at least one threaded pin 254 arranged on the fixating means 152. In an embodiment, several threaded pins 254 are evenly arranged on the ring shaped fixating means 152. Nuts 168 are correspondingly arranged in the adaptor 122, so that removal of the nuts 168 will make the replacement of the filter 136 easy, fast and safe.

FIG. 7 shows a section view in detail of an adaptor 122 according to an embodiment. Fastening elements 154, 254 for connecting the filter to the adaptor are disclosed. On the left hand side in FIG. 7 the fastening element in the shape of a threaded bore 154 is disclosed. The threaded bore 154 is arranged in the fixating means 152 and a threaded bolt 164 fixates the fixating means 152 to the adaptor 122. On the right hand side in FIG. 7 the fastening element in the shape of a threaded pin 254 is disclosed. The threaded pin 254 is arranged on the fixating means 152 and a nut 168 fixates the fixating means 152 to the adaptor 122. The cavities 146 arranged in the ring shaped wall element 140 of the adaptor 122 are clearly disclosed. As mentioned above, the cavities 146 are circumferentially arranged in the periphery of the ring shaped wall element 140 and make it possible to arrange the threaded bolt 164 or nut 168 through the axial directed bores 166 in the adaptor 122. When mounted in the chromatography column 101 the cavities 146 are substantially covered by one of the sliding rings 144, disclosed in FIG. 2.

Figure 8:
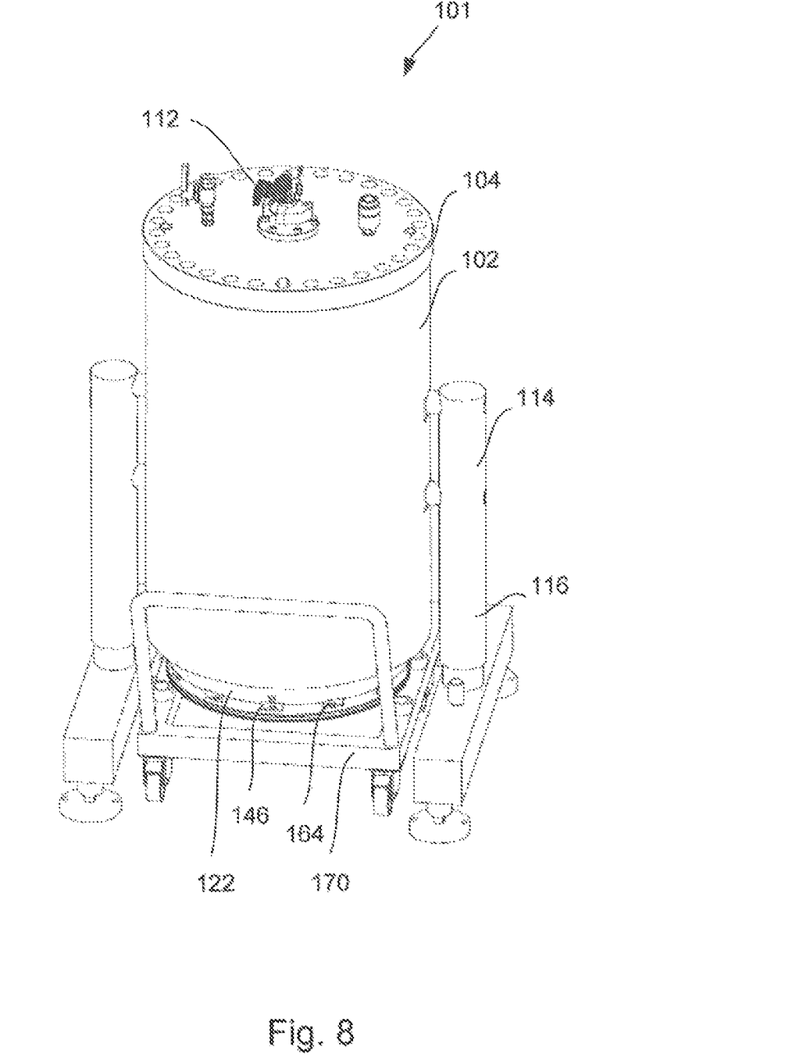
FIG. 8 shows a view in perspective of a chromatography column provided with an adaptor according to the first embodiment of the invention.

FIG. 8 shows a view in perspective of a chromatography column 101 in which the second end unit 106 has been removed and the adaptor 122 has been lowered to a position where a part of the adaptor assembly 122 is still within the tubular housing 102 of the column 101, so that the compression fluid held within the column 101 above the adaptor assembly 122 cannot escape from the column 101. In an embodiment, in this lowered position 122 the first sliding ring 144 of the adaptor assembly 122 is positioned to rest on an inner surface of the tubular housing 102 in order to provide a tight seal between the adaptor assembly 122 and the tubular housing 102. In the first lowered adaptor position the cavities 146 arranged in a periphery of the adaptor assembly 122 are positioned outside the tubular housing 102, so that it is possible to get access to the cavities 146 from outside of the column 101 after removing the second sliding ring 144, which covers the cavities 146. In an embodiment, the cavities 146 are arranged closer to the end surface 141 than to a top surface 143 of the wall element 140 in the axial direction of the adaptor 122. Thereafter the fastening means 164,168 are released trough the cavities 146 for removing the filter 136 from the adaptor assembly 122. A support trolley 170 is arranged under the adaptor 122, so that the filter 136 may rest on the trolley 170 when the filter 136 is removed from the adaptor 122.

Figure 9:
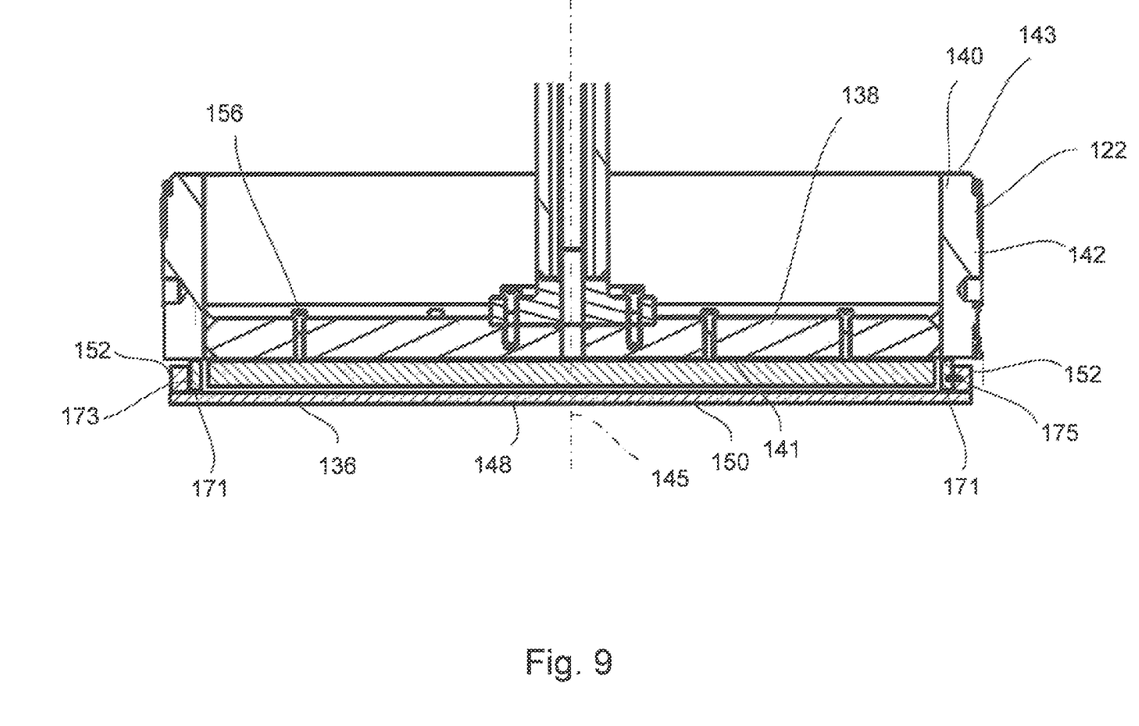
FIG. 9 shows a section view in detail of an adaptor according to a second embodiment of the invention.

FIG. 9 shows a section view in detail of an adaptor 122 according to a second embodiment of the invention. In this embodiment the filter connection arrangement is a flange means 171 arranged on the end surface 141 of bottom plate 138. The flange means 171 extends in the axial direction of the adaptor 122 and is provided with fastening means 173, 175. The fastening means may be a helical thread 173 arranged on the outer periphery of the flange means 171. In the left hand side of FIG. 9 the flange means 171 and the fixating means 152 of the filter are both provided with helical threads 173. The filter 136 is turned in relation to the flange means 171 when mounting or removing the filter 136 to or from the adaptor 122. The fastening means may as an alternative be a bayonet coupling 175 arranged on the outer periphery of the flange means 171. In the right hand side of FIG. 9 the flange means 171 and the fixating means 152 of the filter 136 are both provided with means for obtaining a bayonet coupling. The flange means 171 may be provided with bayonet pins and the fixating means can be provided with bayonet grooves, or vice versa. The filter 136 is turned and axially displaced in relation to the flange means 171 when mounting or removing the filter 136 to or from the adaptor 122.

In all embodiments described above parts and surfaces being in contact with a process fluid are suitably selected from materials that are in accordance with typical material requirements in (bio-)pharmaceutical manufacturing or food grade quality.

For example, materials are suitably in compliance with USP Class VI and/or 21 CFR 177. Furthermore they are suitably of animal-free origin and compliance to EMEA/ 41O/01.

Features and components of the different embodiments above may be combined within the scope of the invention.

The invention claimed is:
1. An adaptor assembly for a chromatography column, comprising:
   an adaptor having:
   (i) at least one threaded device, the threaded device being disposed within a cavity arranged on an outer peripheral wall along a circumference of the adaptor;
   (ii) a filter configured for connection to the adaptor; and
   (iii) at least one fastening device (i) having one end attached to a surface of the filter and another end removably connected to the at least one threaded device and (ii) configured to remove the filter from the adaptor.

2. The adaptor assembly according to claim 1, wherein the adaptor further comprises a bottom plate and a wall element.

3. The adaptor assembly according to claim 2, wherein a threaded bore is arranged between the cavity and an end surface of the bottom plate.

4. The adaptor according to claim 3, wherein the cavity, in the axial direction of the adaptor, is arranged closer to the end surface of the bottom plate than to a top surface of the wall element.

5. The adaptor assembly according to claim 2, wherein the threaded bore extends in a direction substantially parallel to a common axis between the bottom plate and the wall element.

6. The adaptor assembly according to claim 5, wherein in a direction substantially perpendicular to the common axis between the bottom plate and the wall element, the end of the fastening device that is detachably connected to the at least one threaded device is disposed within the cavity.

7. The adaptor according to claim 2, wherein the length of the cavity, in the axial direction of the adaptor, is less than a height of the wall element.

8. The adaptor according to claim 2, wherein the filter comprises a perforated net element and a fixating device attached to the net element, so that a plurality particles and fluid are prevented from passing between the net element and the fixating device, and wherein the fixating device is provided with the at least one fastening device for removably fixating the filter to the adaptor.

9. The adaptor according to claim 8, wherein the fastening device is at least one threaded bore in the fixating device.

10. The adaptor according to claim 9, wherein a threaded bolt is arranged in the cavity and through the threaded bore, the threaded bolt being arranged for connection to the threaded bore in the fixating device.

11. The adaptor according to claim 9, wherein the fastening device is at least one threaded pin arranged on the fixating device.

12. The adaptor according to claim 11, wherein the threaded pin is arranged through the threaded bore and into the cavity, and wherein the threaded pin is arranged to be connected to a nut in the cavity.

13. The adaptor according to claim 8, wherein the fixating device is provided with a sealing surface, which together with a corresponding surface on the adaptor prevents a plurality of particles and fluid from passing between the fixating device and the adaptor.

14. The adaptor according to claim 1, further comprising a plurality of cavities arranged on the outer peripheral along the circumference of the adaptor.

\* \* \* \* \*